United States Patent [19]

Seper et al.

[11] Patent Number: 5,300,201

[45] Date of Patent: Apr. 5, 1994

[54] PHOTOCHLORINATION OF PHTHALIC ANHYDRIDE

[75] Inventors: Karl W. Seper, Youngstown; John R. Molinaro, Kenmore, both of N.Y.

[73] Assignee: Occidental Chemical Corporation, Niagara Falls, N.Y.

[21] Appl. No.: 689,207

[22] Filed: Apr. 22, 1991

[51] Int. Cl.$^5$ .......................................... C07D 307/00
[52] U.S. Cl. .................................................. 204/157.6
[58] Field of Search ............ 204/157.6, 157.69, 157.94

[56] References Cited

U.S. PATENT DOCUMENTS 3,745,103  5/1971  Richtzenhain ................. 260/658 R
4,297,283  10/1981  Verbicky .......................... 260/346.3

FOREIGN PATENT DOCUMENTS 3911951  11/1989  Fed. Rep. of Germany .
3911951A1  11/1989  Fed. Rep. of Germany .

OTHER PUBLICATIONS

Zweig et al. "3-Chlorophthalic Anhydride Through Chlorination of Phthalic Anhydride" American Chemical Society, 1978, p. 3690.

Primary Examiner—John Niebling
Assistant Examiner—C. Delacroix-Muirheid
Attorney, Agent, or Firm—Wayne A. Jones; Richard D. Fuerle

[57] ABSTRACT

Phthalic anhydride can be photochlorinated in the vapor phase to give good yields of 4-chlorophthalic anhydride at temperatures of 250° to 400° C. Optionally, the process can be run to produce di, tri, and tetrachlorophthalic anhydrides.

20 Claims, No Drawings

PHOTOCHLORINATION OF PHTHALIC ANHYDRIDE

BACKGROUND OF THE INVENTION

The present invention relates to a method for chlorinating phthalic anhydride. More specifically, it relates to a method of photochlorinating phthalic anhydride vapor.

Several methods have been employed for direct chlorination of phthalic anhydride using chlorine. U.S. Pat. No. 4,297,283 reports that both phthalic anhydride and orthophthalonitrile may be chlorinated in the vapor phase using chlorine gas at temperatures above 350° C., and usually below 600° C. The optimum temperature is said to be between 350° and 475° C. The 4-chloro isomer is a favored product and the molar ratio of the 4-chloro to the 3-chloro compound ranges between 5 and 11. It is preferred to use an inert gas carrier such as nitrogen or helium, etc. in the reaction chamber. It is also preferred to use a molar excess of chlorine over the aromatic compound of between 0.5 to 20 moles of chlorine per mole of aromatic compound.

German patent DE 3,911,951, discloses a process for preparing chlorophthalates by chlorinating the parent compounds, in the gas phase, at a temperature range in from 300° to 700° C. The chlorine to substrate ratio is between 0.7:1 to 5:1 and the process employs activated carbon catalyst prepared by doping activated charcoal, zeolite, alumina, or silica with a metal salt or oxide from the first, second or eighth sub groups. In the chlorination of phthalic anhydride, the best example presented reaction product consisting of 70% 4-chlorophthalic anhydride, 1% 3-chlorophthalic anhydride, 3% dichlorophthalic anhydride, and 23% unreacted phthalic anhydride.

Japanese patent 62185082, as abstracted in CA 108:95092s, discloses the gas phase chlorination of phthalic anhydride in the presence of a catalyst consisting of iron compounds and activated carbon to produce tetrachlorophthalic anhydride. The process is conducted at a temperature of approximately 320° C.

Japanese patent 60161974, as abstracted in CA 104:89172u, discloses the gas phase reaction of phthalic anhydride with chlorine at a temperature range of 200°-400° C. to form tetrachlorophthalic anhydride in the presence of a catalyst composed of $CoCl_2$ and a component selected from $CaCl_2$, $BaCl_2$, and $LaCl_3$, all deposited on active carbon.

The photochlorination of aromatic compounds is not always predictable. For example, U.S. Pat. No. 2,499,120 discloses that a mixture of benzene and chlorine may be photochlorinated to produce predominately the gamma isomer of hexachlorocyclohexane.

U.S. Pat. No. 4,268,457 discloses that photochlorination of paraphenoxytoluene produces chlorination on the side chain rather than on the ring. Accordingly, the product of the chlorination is paraphenoxybenzotrichloride.

U.S. Pat. No. 4,046,656 discloses that bromine acts as a catalyst in the photochlorination of methyl-substituted aromatic compounds. In this photochlorination process, all chlorines substitute on the methyl group, while the ring hydrogens are considered inert substituents, that is, they are not readily displaced by chlorine.

U.S. Pat. No. 4,643,811 discloses a photochemical process for the preparation of 1,1-dichloro-2,2,2-trifluoroethoxybenzene derivatives. The process involves photochlorination of 2,2,2-trifluoroethoxybenzene derivatives. The chlorination occurs at the α-carbon of the ethoxy side chain, rather than on the ring.

Zweig and Epstein (J. Org. Chem. vol. 43, p. 3690, 1978 (at page 3691)) report that as part of another research effort, they attempted to induce the liquid phase chlorination of phthalic anhydride using ultraviolet radiation. They report that the reaction could not be induced by ultraviolet irradiation at temperatures up to 235° C.

SUMMARY OF THE INVENTION

Surprisingly, we have now found that phthalic anhydride can be photochlorinated in the vapor phase to give good yields of 4-chlorophthalic anhydride at temperatures of 250° to 400° C. Optionally, the process can be run under more vigorous conditions to produce di, tri, and tetrachlorophthalic anhydride.

DETAILED DESCRIPTION OF THE INVENTION

This invention relates to a process for forming 4-chlorophthalic anhydride. (4CPAN) is a useful intermediate for the formation of diphthalic anhydrides. For example, 4-chlorophthalic anhydride can be used to form 4,4'-oxydiphthalic anhydride as disclosed in U.S. Pat. No. 4,697,023. Dianhydrides in turn are useful for the preparation of polyimide resins, which are particularly useful because of their high temperature resistance and good electrical properties. However, the presence of (3CPAN) as an impurity in 4-chlorophthalic anhydride is not desirable when preparing polyimide resins.

It is an object of the present invention to provide a process which yields 4-chlorophthalic anhydride with relatively little contamination of the 3-chloro isomer. It is also an object of the present invention to provide a process for the production of 4-chlorophthalic anhydride which can be conducted with relatively moderate ratios of chlorine to (PAN), and which does not require the presence of a solid catalyst. It is a further object of the invention to provide a process for the production of di, tri, and tetrachlorophthalic anhydrides.

Surprisingly, we have discovered that photochlorination of phthalic anhydride vapor proceeds to produce 4-chlorophthalic anhydride with very little contamination of 3-chlorophthalic anhydride. The advantages of the instant process are that it does not require any catalyst, it can be conducted at moderate temperatures and it does not require large excesses of chlorine. As further set forth below, under more vigorous conditions, di, tri, and tetrachlorophthalic anhydride can be produced.

In the process of Applicants' invention, phthalic anhydride vapor is mixed with chlorine gas, and the mixture is conducted to a heated reaction chamber. The reaction mixture is irradiated with light, and the resulting reaction mixture is cooled and fractionated to yield the desired products. The source of light for irradiation can be either incandescent light or ultraviolet light. As used herein, the term "light" shall mean (UV) or visible light. Ultraviolet is preferred for illumination, since its use generally results in better yields. The importance of illuminating the reaction mixture is illustrated by Example 2 in which runs were conducted under similar conditions with and without ultraviolet illumination. With ultraviolet illumination, conversion of approximately 90% was achieved. In a very similar run without illumination, the conversion was 0.2%. This result indicates that this process is a true photochlorination since the reaction does not occur when the reactants are heated in the dark but does occur in the presence of the illumination.

Depending on conditions, the 4-chlorophthalic anhydride to 3-chlorophthalic anhydride molar ratio may vary between 5:1 to 11:1. The reaction can be conducted at temperatures of 250° to 400° C. As set forth below, the preferred temperature range depends upon the product mixture that one wishes to produce.

The process can be run at a wide variety of molar ratios of chlorine to phthalic anhydride. However, large excesses of chlorine are not required and are not desirable because of the expense of separating excess chlorine from the HCl found in the chlorination reaction. To produce monochlorophthalic anhydride, the preferred ratio of chlorine to phthalic anhydride is between about 1:1 to 4:1. To produce di, tri, or tetrachlorophthalic anhydrides, higher ratios of chlorine to phthalic acid are preferred. A diluent gas can be used but is not required.

An inert diluent gas can be mixed with the phthalic anhydride and chlorine vapors. The order of mixing is not critical. Thus, the same effect is achieved by mixing the inert gas with either the phthalic anhydride or chlorine prior to forming the final mixture. Alternatively, the phthalic anhydride, chlorine and inert gas can be mixed in a single step. A wide variety of inert gas diluents can be used. The major requirement for such a gas is that it be unreactive toward chlorine and phthalic anhydride. Suitable inert diluents include helium, nitrogen, argon and halogenated organics that are not reactive with chlorine. Nitrogen is the least costly diluent and therefore, preferred if a diluent is to be used. However, the presence of a diluent gas tends to reduce the percentage of phthalic anhydride converted to products, and also to decrease the ratio of 4-chlorophthalic anhydride to 3-chlorophthalic anhydride. On the other hand, the presence of a diluent gas cuts down the amount of dichloro and higher chlorophthalic anhydrides produced. Accordingly, although inert diluents can be used, it is preferred to run the reaction without any diluent.

As the temperature of the reaction is increased, one obtains higher conversions of phthalic anhydride to chlorinated products. The ratio of 4-chlorophthalic anhydride to 3-chlorophthalic anhydride does not necessarily suffer as the temperature is raised. However, higher temperature reactions tend to produce more dichlorinated and trichlorinated products than are produced in lower temperature reactions. For example, a reaction run at 400° C. may produce 25-30% dichlorophthalic anhydride while a reaction run at 250° C. will produce a much smaller percentage of dichlorophthalic anhydride. Reactions run at higher conversion of phthalic anhydride to chlorinated derivatives tend to produce higher yields of di, tri, and tetrachlorophthalic anhydrides.

It is possible to use the process of this invention to produce tetrachlorophthalic anhydride. To do this, one must use a ratio of chlorine to phthalic anhydride of at least 4:1 and preferably about 16:1. In addition, a higher powered lamp is required, and optionally, the residence time of the reactant within the reactor can be increased. Residence time can be increased by slowing the flow rate or increasing the volume of the reactor. When the reactor volume is increased, care must be taken to assure proper mixing and even illumination. Methods of accomplishing these goals are well-known to those skilled in the art. If sufficiently vigorous conditions are selected, tetrachlorophthalic anhydride can be produced as the major product. Under less vigorous conditions, a mixture of mono, di, tri and tetrachlorophthalic anhydrides will be produced. However, whatever product is produced within the monochlorophthalic anhydride product stream, the 4-chlorophthalic anhydride will be the predominant product.

Mixtures of unreacted phthalic anhydride, monochlorophthalic anhydride, and higher chlorinated phthalic anhydrides can be readily separated by distillation, provided that the ratio of 4-chlorophthalic anhydride to 3-chlorophthalic anhydride is in the range of 5:1 or above. Quantities of dichlorophthalic anhydride as high as 30% of the reaction mixture can be separated by distillation methods well known to those skilled in the art. The best mode for running the reaction varies depending upon several factors. If dichlorophthalic acid is a useful product, it may be desirable to run the reaction at higher conversions and produce larger amounts of dichlorophthalic anhydride. On the other hand, if dichlorophthalic anhydride represents a waste product that must be disposed of, it may be desirable to run the reaction at lower conversions and accept the burden of recycling a higher percentage of phthalic anhydride.

If the process is conducted in such a manner as to produce appreciable quantities of tetrachlorophthalic anhydride, this can readily be separated from the other products of the reaction since it has a higher boiling point and can be recovered as a still bottom and then further purified by methods well-known to those skilled in the art. As an alternative to separating all the products of the reaction, it is possible to conduct the process so that the reaction product is separated into three streams. The first stream would be a monochlorophthalic anhydride stream, the second stream would be the tetrachlorophthalic anhydride stream and the third stream would be a mixture of chlorophthalic anhydrides. This mixture would be predominantly di and trichlorophthalic anhydrides but, depending upon the method of separation, may include some monochloro and tetrachlorophthalic anhydride. Instead of separating this mixture into individual compounds, one could use the mixture as a starting material for the production of phthalocyanine dyes.

The reaction is conducted by heating phthalic acid to form the vapor, mixing the vapor with chlorine and conducting the combined vapor to a heated photolysis chamber. As indicated above, a diluent gas such as nitrogen can be used but is not the preferred method of practicing the invention. One method of using the diluent gas is to mix it with the chlorine prior to the reaction. Another method of using the diluent gas is to use it to drive the phthalic anhydride vapor into the reactor. For example, a diluent gas, such as nitrogen, can be bubbled through a pot of molten phthalic anhydride and then the combined nitrogen-phthalic anhydride vapor can be mixed with chlorine and conducted to the reaction chamber.

A particularly simple method of mixing the phthalic anhydride vapor with chlorine is to warm the phthalic anhydride to a temperature between about 200° and 270° C. Chlorine gas, preheated to 80° to 250° C., is then bubbled through the hot liquid phthalic anhydride. Little reaction occurs in the liquid phase and the chlorine gas carries phthalic anhydride vapors into the photolysis reactor.

A wide variety of photolysis reactors can be used in practicing this process. For example, the Kirk-Othmer Encyclopedia of Technology (3rd edition, Volume 17 pp. 540-559) shows a number of photolysis reactors that could be used in the present process. The person skilled in the art would have little difficulty picking a photolysis reactor for this process.

A wide variety of sources can be used to irradiate the reaction chamber. If visible light is chosen for the photolysis, one can use ordinary incandescent lamps, high intensity incandescent light sources, such as those used in projection systems, or even carbon arc lamps. If ultraviolet light is chosen for photolysis, there is an equally wide variety of light sources to choose from. For example, various sorts of arc lamps can be used. Among the most convenient sources are mercury lamps. The selection of lamps depends largely upon the scale of the reaction. The higher the light output of the lamp in question, the faster the reaction proceeds. Accordingly, higher output lamps allow higher speed reactors. Using ultraviolet illumination, at a reactant flow rate of about 3 millimoles per minute of phthalic anhydride, we have found that lamps ranging in size from a 2.4 watt input low pressure mercury lamp to a 100 watt input medium pressure mercury lamp are adequate. If one scales up the reaction, one would scale up the lamp size as well.

EXAMPLES

Example 1

Phthalic anhydride (73.0 g, 0.50 mol) was charged to the vaporizer and warmed to between 240°-280° C. Chlorine gas, preheated to 80° C. was bubbled through the hot, liquid phthalic anhydride. This process was continued until the phthalic anhydride was substantially consumed. The vapor mixture of $Cl_2$ and phthalic anhydride was passed into a quartz hot tube (30.5 cm long, 2.5 cm. i.d.). Because of the thermocouple well and quartz chips contained in the reactor, the effective internal value is 93 $cm^3$. The reactor was heated to the desired temperature by means of a split tube furnace or heating tape. GC (gas chromatograph) analyses were performed on 5 separate fractions of the reactor effluent to insure steady state conditions had been achieved. The chlorine flow rate was 200 SCCM (standard cubic centimeters per minute) in all experiments. In this particular experimental setup, the ratio of phthalic anhydride to chlorine is controlled by the temperature of the phthalic anhydride reservoir. The higher the temperature in the reservoir, the higher vapor pressure of the phthalic anhydride and the lower the ratio of chlorine to phthalic anhydride. At 240° C., the ratio is approximately 2.6:1; at 270° C., the ratio is approximately 1.4:1; and at 280° C., it is approximately 1.1:1. A 2.4 watt input lamp was used for all experiments. The results are shown in the following table.

Example 2

Example 2 was run under conditions similar to that for Example 1. Part A was run in the presence of a 2.4 watt input ultraviolet lamp; Part B was run in the absence of an ultraviolet lamp.

Example 3

Reactions were run under conditions similar to those for Example 1. Experiment A was conducted with a 2.4 watt input lamp and Experiment B was conducted with a 100 watt input lamp.

Example 4

An experiment was conducted under the conditions of Example 1 with the exception that in Experiments B-E the chlorine was diluted with nitrogen prior to being bubbled through the heated phthalic anhydride. In Experiment A there was no nitrogen diluent. All experiments were conducted with a 100 watt input ultraviolet lamp.

| COMPOSITION OF REACTION PRODUCT | | | | | | | | | | |
|---|---|---|---|---|---|---|---|---|---|---|
| Exp. # | Phthalic Vaporizer Temp. | Reactor Temp. | Conversion | Selectivity | PAN | 4CPAN | 3CPAN | 4 to 3 Ratio | Dichloro PAN | Trichloro PAN |
| EXAMPLE 1 | | | | | | | | | | |
| A | 240.00 | 250.00 | 14.70 | 87.47 | 85.21 | 12.84 | 1.52 | 8.45 | 0.32 | 0.00 |
| B | 240.00 | 350.00 | 54.99 | 80.32 | 45.01 | 44.16 | 6.24 | 7.08 | 4.58 | 0.00 |
| C | 240.00 | 375.00 | 89.66 | 66.12 | 10.28 | 58.92 | 5.53 | 10.65 | 23.46 | 1.20 |
| D | 240.00 | 400.00 | 92.67 | 62.37 | 7.33 | 57.80 | 6.05 | 9.55 | 27.11 | 1.72 |
| E | 280.00 | 300.00 | 54.16 | 73.59 | 43.85 | 38.12 | 4.18 | 9.12 | 9.17 | 0.33 |
| EXAMPLE 2 | | | | | | | | | | |
| A | 270.00 | 375.00 | 89.66 | 66.12 | 10.28 | 58.92 | 5.53 | 10.65 | 23.46 | 1.20 |
| B | 270.00 | 380.00 | 0.20 | 50.00 | 99.70 | 0.10 | 0.10 | 1.00 | 0.00 | 0.00 |

| Exp. # | UV Wattage | Vaporizer Temp. | Reactor Temp. | Conversion | Selectivity | PAN | 4CPAN | 3CPAN | 4 to 3 Ratio | Dichloro PAN | Trichloro PAN | TETRA CHLOR |
|---|---|---|---|---|---|---|---|---|---|---|---|---|
| EXAMPLE 3 | | | | | | | | | | | | |
| A | 2.40 | 270.00 | 280.00 | 14.70 | 87.47 | 85.21 | 12.84 | 1.52 | 8.45 | 0.32 | 0.00 | 0.00 |
| B | 11.40 | 270.00 | 285.00 | 96.87 | 24.24 | 3.04 | 20.03 | 1.83 | 10.95 | 36.59 | 24.19 | 11.30 |

| Exp. # | % Chlorine | Vaporizer Temp. | Reactor Temp. | Conversion | Selectivity | PAN | 4CPAN | 3CPAN | 4 to 3 Ratio | Dichloro PAN | Trichloro PAN | TETRA CHLOR |
|---|---|---|---|---|---|---|---|---|---|---|---|---|
| EXAMPLE 4 | | | | | | | | | | | | |
| A | 100.00 | 270.00 | 270.00 | 96.87 | 24.24 | 3.04 | 20.03 | 1.83 | 10.95 | 36.59 | 24.19 | 11.30 |
| B | 80.00 | 270.00 | 280.00 | 54.77 | 64.77 | 45.16 | 35.42 | 6.49 | 5.46 | 11.45 | 1.33 | 0.00 |
| C | 67.00 | 270.00 | 275.00 | 29.19 | 75.99 | 70.73 | 22.16 | 4.34 | 5.11 | 2.59 | 0.07 | 0.00 |
| D | 67.00 | 270.00 | 275.00 | 29.19 | 75.99 | 79.73 | 22.16 | 4.34 | 5.11 | 2.59 | 0.07 | |

| | | | COMPOSITION OF REACTION PRODUCT | | | | | | | |
|---|---|---|---|---|---|---|---|---|---|---|
| E | 67.00 | 270.00 | 350.00 | 56.78 | 61.09 | 42.17 | 33.85 | 6.03 | 5.61 | 13.66 | 1.87 |

PAN = phthalic anhydride,
CPAN = chlorophthalic anhydride

Example 5

Following the procedure of Example 1, two 75 watt floodlamps were used as a light source. The results are shown in the following table.

| Exp. # | Pot °C. | React. °C. | PAN | 4CPAN | 3CPAN | di's | Conv. | Sel. | Yield |
|---|---|---|---|---|---|---|---|---|---|
| A | 260 | 325 | 85.2 | 12.7 | 1.6 | .3 | 14.8 | 90 | 13 |
| B | 260 | 375 | 46.8 | 38.4 | 6.3 | 7.3 | 54 | 72 | 39 |

We claim:

1. A process for reacting chlorine with phthalic anhydride to produce a product mixture of 4-chlorophthalic anhydride and 3-chlorophthalic anhydride in a molar ratio of at least 5 to 1 comprising
   (A) passing a reactant mixture of chlorine and phthalic anhydride in a molar ratio of about 1.1:1 to about 16:1 in the vapor phase into a reaction chamber; and
   (B) irradiating said reactant mixture with light.
2. A process according to claim 1 in which said light is ultraviolet light.
3. A process according to claim 1 conducted at a temperature of 250° to 400° C.
4. A process according to claim 3 conducted at a temperature of 275° to 325° C.
5. A process according to claim 1 wherein an inert diluent gas is included in said reactant mixture.
6. A process according to claim 5 wherein said diluent gas is nitrogen.
7. A process according to claim 5 wherein said reactant mixture does not include a diluent gas.
8. A process according to claim 1 in which the light irradiating the contents of the reaction chamber is visible light.
9. A process according to claim 1, including the additional last step of separating said product mixture into a monochlorophthalic anhydride product and a di, tri, and tetrachlorophthalic anhydride product.
10. A process according to claim 9 wherein said di, tri, and tetra chlorophthalic anhydride product is further separated into a product comprising a mixture of di and trichlorophthalic anhydrides and a product comprising tetrachlorophthlic anhydride.
11. A process according to claim 1 wherein said molar ratio of chlorine to phthalic anhydride is between about 1.1:1 and 4:1.
12. A process according to claim 11 wherein said molar ratio of chlorine to phthalic anhydride is between about 1:1 and 2:1.
13. A process according to claim 1 wherein said molar ratio of chlorine to phthalic anhydride is between 4:1 and 16:1.
14. A process according to claim 13 with the additional step of isolating tetrachlorophthalic anhydride from said chlorinated phthalic anhydride product.
15. A process according to claim 14 with the additional step of isolating from said chlorinated phthalic anhydride product a product comprising a mixture of di and trichlorophthalic anhydrides.
16. A process according to claim 14 with the additional steps of isolating from said chlorinated phthalic anhydride product a product comprising dichlorophthalic anhydride and a product comprising trichlorophthalic anhydride.
17. A method of making 4-chlorophthalic anhydride comprising
   (A) preparing a mixture of chlorine and phthalic anhydride in a molar ratio of about 1.1:1 to about 4:1 in a vapor phase at a temperature of 250° to 400° C.;
   (B) exposing said mixture to light in the absence of a catalyst; and
   (C) separating said 4-chlorophthalic anhydride from said mixture.
18. A method according to claim 17 wherein said light is ultraviolet light.
19. A method according to claim 17 wherein said 4-chlorophthalic anhydride is separated by distillation.
20. A method of making a mixture of 4-chlorophthalic anhydride and 3-chlorophthalic anhydride in a molar ratio of at least 5:1 comprising
   (A) preparing a mixture consisting of chlorine and phthalic anhydride in a molar ratio between 1 to 1 and 2 to 1;
   (B) heating said mixture to form a vapor at a temperature of 275° to 325° C.;
   (C) exposing said mixture to at least 100 watts of ultraviolet light; and
   (D) distilling said mixture to recover said 4-chlorophthalic anhydride therefrom.

* * * * *